(12) United States Patent
Frion et al.

(10) Patent No.: US 8,512,404 B2
(45) Date of Patent: Aug. 20, 2013

(54) OCULAR IMPLANT DELIVERY SYSTEM AND METHOD

(75) Inventors: Duane Frion, Brooklyn Center, MN (US); Rebecca McCarville, Spring Park, MN (US); Andrew T. Schieber, Golden Valley, MN (US); Nathaniel Zenz-Olson, Blaine, MN (US); Diane Feehan, Corcoran, MN (US); Edward Matthees, Minneapolis, MN (US); Charles L. Euteneuer, St. Michael, MN (US)

(73) Assignee: Ivantis, Inc., Irvine, CA (US)

( * ) Notice: Subject to any disclaimer, the term of this patent is extended or adjusted under 35 U.S.C. 154(b) by 766 days.

(21) Appl. No.: 11/943,289

(22) Filed: Nov. 20, 2007

(65) Prior Publication Data

US 2009/0132040 A1    May 21, 2009

(51) Int. Cl.
*A61F 2/16* (2006.01)

(52) U.S. Cl.
USPC ........................................ 623/6.12

(58) Field of Classification Search
USPC .................... 623/6.11, 6.12, 6.13, 6.14, 1.11; 606/107, 108, 166
See application file for complete search history.

(56) References Cited

U.S. PATENT DOCUMENTS

| | | | |
|---|---|---|---|
| 3,788,327 A | 1/1974 | Donowitz et al. | |
| 3,948,271 A * | 4/1976 | Akiyama | 604/540 |
| 4,037,604 A | 7/1977 | Newkirk | |
| 4,428,746 A | 1/1984 | Mendez | |
| 4,457,757 A | 7/1984 | Molteno | |
| 4,722,724 A | 2/1988 | Schocket | |
| 4,733,665 A | 3/1988 | Palmaz | |
| 4,750,901 A | 6/1988 | Molteno | |
| 4,826,478 A | 5/1989 | Schocket | |
| 4,886,488 A | 12/1989 | White | |
| 4,934,809 A | 6/1990 | Volk | |
| 4,936,825 A | 6/1990 | Ungerleider | |

(Continued)

FOREIGN PATENT DOCUMENTS

| | | |
|---|---|---|
| AU | 1998/76197 B2 | 2/1999 |
| CN | 1950091 A | 4/2007 |

(Continued)

OTHER PUBLICATIONS

U.S. Appl. No. 60/131,030, filed Apr. 26, 1999, Lynch.

(Continued)

*Primary Examiner* — Ryan Severson
*Assistant Examiner* — Jonathan W Miles
(74) *Attorney, Agent, or Firm* — Shay Glenn LLP

(57) ABSTRACT

A method of inserting an ocular implant into a patient's eye, the ocular implant being mounted on a carrier, the method comprising: inserting a cannula into an anterior chamber of the eye; moving a distal exit port of the cannula into communication with Schlemm's canal; and advancing the ocular implant and carrier through an exit port of the cannula into Schlemm's canal. The invention also provides an ocular implant and delivery system comprising: a cannula comprising a distal exit port adapted to be inserted into a Schlemm's canal portion of an eye; an ocular implant; a carrier disposed within the implant and movable with the implant within the cannula; and a proximal control adapted to be operated from exterior to an eye to move at least one of the carrier and the implant when the distal exit port of the cannula is within the eye.

24 Claims, 14 Drawing Sheets

(56) References Cited

U.S. PATENT DOCUMENTS

| | | |
|---|---|---|
| 4,946,436 A | 8/1990 | Smith |
| 4,968,296 A | 11/1990 | Ritch et al. |
| 5,092,837 A * | 3/1992 | Ritch et al. ............... 604/8 |
| 5,127,901 A | 7/1992 | Odrich |
| 5,178,604 A | 1/1993 | Baerveldt et al. |
| 5,180,362 A | 1/1993 | Worst |
| 5,213,569 A | 5/1993 | Davis |
| 5,246,452 A | 9/1993 | Sinnott |
| 5,360,399 A | 11/1994 | Stegmann |
| 5,372,577 A | 12/1994 | Ungerleider |
| 5,454,796 A | 10/1995 | Krupin |
| 5,458,615 A * | 10/1995 | Klemm et al. ............... 606/198 |
| 5,591,223 A | 1/1997 | Lock et al. |
| 5,626,558 A | 5/1997 | Suson |
| 5,792,099 A | 8/1998 | DeCamp et al. |
| 5,807,302 A | 9/1998 | Wandel |
| 5,865,831 A | 2/1999 | Cozean et al. |
| 5,868,697 A | 2/1999 | Richter et al. |
| 5,879,319 A | 3/1999 | Pynson et al. |
| 5,893,837 A | 4/1999 | Eagles et al. |
| 5,948,427 A | 9/1999 | Yamamoto et al. |
| 5,968,058 A | 10/1999 | Richter et al. |
| 6,007,511 A | 12/1999 | Prywes |
| 6,050,970 A | 4/2000 | Baerveldt |
| 6,102,045 A | 8/2000 | Nordquist et al. |
| 6,186,974 B1 | 2/2001 | Allan et al. |
| 6,221,078 B1 | 4/2001 | Bylsma |
| 6,238,409 B1 | 5/2001 | Hojeibane |
| D444,874 S | 7/2001 | Haffner et al. |
| 6,375,642 B1 | 4/2002 | Grieshaber et al. |
| 6,409,752 B1 | 6/2002 | Boatman et al. |
| 6,450,984 B1 | 9/2002 | Lynch et al. |
| 6,464,724 B1 * | 10/2002 | Lynch et al. ............... 623/4.1 |
| 6,471,666 B1 | 10/2002 | Odrich |
| 6,494,857 B1 | 12/2002 | Neuhann |
| 6,508,779 B1 | 1/2003 | Suson |
| 6,524,275 B1 | 2/2003 | Lynch et al. |
| 6,533,764 B1 | 3/2003 | Haffner et al. |
| 6,533,768 B1 | 3/2003 | Hill |
| 6,544,208 B2 | 4/2003 | Ethier et al. |
| 6,544,249 B1 | 4/2003 | Yu et al. |
| 6,626,858 B2 | 9/2003 | Lynch et al. |
| 6,638,239 B1 | 10/2003 | Bergheim et al. |
| 6,666,841 B2 | 12/2003 | Gharib et al. |
| 6,699,210 B2 | 3/2004 | Williams et al. |
| 6,699,211 B2 | 3/2004 | Savage |
| 6,726,676 B2 | 4/2004 | Stegmann et al. |
| D490,152 S | 5/2004 | Myall et al. |
| 6,730,056 B1 | 5/2004 | Ghaem et al. |
| 6,736,791 B1 | 5/2004 | Tu et al. |
| 6,780,164 B2 | 8/2004 | Bergheim et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,881,198 B2 | 4/2005 | Brown |
| 6,939,298 B2 | 9/2005 | Brown et al. |
| 6,955,656 B2 | 10/2005 | Bergheim et al. |
| 6,962,573 B1 | 11/2005 | Wilcox |
| 6,981,958 B1 | 1/2006 | Gharib et al. |
| 6,989,007 B2 | 1/2006 | Shadduck |
| 7,094,225 B2 | 8/2006 | Tu et al. |
| 7,135,009 B2 | 11/2006 | Tu et al. |
| 7,147,650 B2 | 12/2006 | Lee |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,207,965 B2 | 4/2007 | Simon |
| 7,207,980 B2 | 4/2007 | Christian et al. |
| 7,220,238 B2 | 5/2007 | Lynch et al. |
| 7,273,475 B2 | 9/2007 | Tu et al. |
| 7,297,130 B2 | 11/2007 | Bergheim et al. |
| 7,331,984 B2 | 2/2008 | Tu et al. |
| 7,699,882 B2 | 4/2010 | Stamper et al. |
| 7,931,596 B2 | 4/2011 | Rachlin et al. |
| 7,967,772 B2 | 6/2011 | McKenzie et al. |
| 8,012,115 B2 | 9/2011 | Karageozian |
| 8,034,105 B2 | 10/2011 | Stegmann et al. |
| 8,123,729 B2 | 2/2012 | Yamamoto et al. |
| 8,372,026 B2 | 2/2013 | Schieber et al. |
| 2001/0002438 A1 | 5/2001 | Sepetka et al. |
| 2002/0003546 A1 | 1/2002 | Mochimaru et al. |
| 2002/0013546 A1 | 1/2002 | Grieshaber et al. |
| 2002/0013572 A1 | 1/2002 | Berlin |
| 2002/0072673 A1 | 6/2002 | Yamamoto et al. |
| 2002/0133168 A1 | 9/2002 | Smedley et al. |
| 2002/0143284 A1 | 10/2002 | Tu et al. |
| 2003/0004457 A1 | 1/2003 | Andersson |
| 2003/0055372 A1 | 3/2003 | Lynch et al. |
| 2003/0060748 A1 | 3/2003 | Baikoff |
| 2003/0060752 A1 | 3/2003 | Bergheim et al. |
| 2003/0093084 A1 | 5/2003 | Nissan et al. |
| 2003/0097151 A1 | 5/2003 | Smedley et al. |
| 2003/0181848 A1 | 9/2003 | Bergheim et al. |
| 2003/0187384 A1 | 10/2003 | Bergheim et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0024345 A1 | 2/2004 | Gharib et al. |
| 2004/0024453 A1 | 2/2004 | Castillejos |
| 2004/0082939 A1 * | 4/2004 | Berlin ............... 606/5 |
| 2004/0088048 A1 | 5/2004 | Richter et al. |
| 2004/0098124 A1 | 5/2004 | Freeman et al. |
| 2004/0102729 A1 | 5/2004 | Haffner et al. |
| 2004/0106975 A1 | 6/2004 | Solovay et al. |
| 2004/0111050 A1 | 6/2004 | Smedley et al. |
| 2004/0127843 A1 | 7/2004 | Tu et al. |
| 2004/0147870 A1 | 7/2004 | Burns et al. |
| 2004/0193095 A1 | 9/2004 | Shadduck |
| 2004/0193262 A1 | 9/2004 | Shadduck |
| 2004/0210181 A1 | 10/2004 | Vass et al. |
| 2004/0210185 A1 | 10/2004 | Tu et al. |
| 2004/0216749 A1 | 11/2004 | Tu |
| 2004/0225357 A1 | 11/2004 | Worst et al. |
| 2004/0249333 A1 | 12/2004 | Bergheim et al. |
| 2004/0254519 A1 | 12/2004 | Tu et al. |
| 2004/0254520 A1 | 12/2004 | Porteous et al. |
| 2004/0260228 A1 | 12/2004 | Lynch et al. |
| 2005/0041200 A1 | 2/2005 | Rich |
| 2005/0049578 A1 | 3/2005 | Tu et al. |
| 2005/0090806 A1 | 4/2005 | Lynch et al. |
| 2005/0090807 A1 | 4/2005 | Lynch et al. |
| 2005/0101967 A1 | 5/2005 | Weber et al. |
| 2005/0107734 A1 | 5/2005 | Coroneo |
| 2005/0119601 A9 | 6/2005 | Lynch et al. |
| 2005/0119636 A1 | 6/2005 | Haffner et al. |
| 2005/0125003 A1 | 6/2005 | Pinchuk et al. |
| 2005/0131514 A1 | 6/2005 | Hijlkema et al. |
| 2005/0154443 A1 | 7/2005 | Linder et al. |
| 2005/0165385 A1 | 7/2005 | Simon |
| 2005/0192527 A1 | 9/2005 | Gharib et al. |
| 2005/0197667 A1 | 9/2005 | Chan et al. |
| 2005/0203542 A1 | 9/2005 | Weber et al. |
| 2005/0209549 A1 | 9/2005 | Bergheim et al. |
| 2005/0209550 A1 | 9/2005 | Bergheim et al. |
| 2005/0244464 A1 | 11/2005 | Hughes |
| 2005/0250788 A1 | 11/2005 | Tu et al. |
| 2005/0260186 A1 | 11/2005 | Bookbinder et al. |
| 2005/0266047 A1 | 12/2005 | Tu et al. |
| 2005/0271704 A1 | 12/2005 | Tu et al. |
| 2005/0273033 A1 | 12/2005 | Grahn et al. |
| 2005/0277864 A1 | 12/2005 | Haffner et al. |
| 2005/0288619 A1 | 12/2005 | Gharib et al. |
| 2005/0288745 A1 | 12/2005 | Andersen et al. |
| 2006/0020247 A1 | 1/2006 | Kagan et al. |
| 2006/0032507 A1 | 2/2006 | Tu |
| 2006/0052879 A1 | 3/2006 | Kolb |
| 2006/0069340 A1 | 3/2006 | Simon |
| 2006/0074375 A1 | 4/2006 | Bergheim et al. |
| 2006/0079828 A1 | 4/2006 | Brown |
| 2006/0084907 A1 | 4/2006 | Bergheim et al. |
| 2006/0106370 A1 | 5/2006 | Baerveldt et al. |
| 2006/0116626 A1 | 6/2006 | Smedley et al. |
| 2006/0149194 A1 | 7/2006 | Conston et al. |
| 2006/0154981 A1 | 7/2006 | Klimko et al. |

| | | | |
|---|---|---|---|
| 2006/0155238 A1 | 7/2006 | Shields | |
| 2006/0155300 A1 | 7/2006 | Stamper et al. | |
| 2006/0173397 A1 | 8/2006 | Tu et al. | |
| 2006/0189915 A1 | 8/2006 | Camras et al. | |
| 2006/0189916 A1 | 8/2006 | Bas et al. | |
| 2006/0189917 A1 | 8/2006 | Mayr et al. | |
| 2006/0195055 A1 | 8/2006 | Bergheim et al. | |
| 2006/0195056 A1 | 8/2006 | Bergheim et al. | |
| 2006/0195187 A1 | 8/2006 | Stegmann et al. | |
| 2006/0200113 A1 | 9/2006 | Haffner et al. | |
| 2006/0241749 A1 | 10/2006 | Tu et al. | |
| 2007/0010827 A1 | 1/2007 | Tu et al. | |
| 2007/0073275 A1 | 3/2007 | Conston et al. | |
| 2007/0088432 A1 | 4/2007 | Solovay et al. | |
| 2007/0106200 A1 | 5/2007 | Levy | |
| 2007/0106236 A1 | 5/2007 | Coroneo | |
| 2007/0112292 A1 | 5/2007 | Tu et al. | |
| 2007/0118147 A1 | 5/2007 | Smedley et al. | |
| 2007/0179520 A1 | 8/2007 | West | |
| 2007/0191863 A1 | 8/2007 | De Juan, Jr. et al. | |
| 2007/0202186 A1 | 8/2007 | Yamamoto et al. | |
| 2007/0265582 A1 | 11/2007 | Kaplan et al. | |
| 2007/0270945 A1* | 11/2007 | Kobayashi et al. | 623/6.12 |
| 2007/0276315 A1 | 11/2007 | Haffner et al. | |
| 2007/0276316 A1 | 11/2007 | Haffner et al. | |
| 2007/0282244 A1 | 12/2007 | Tu et al. | |
| 2007/0282245 A1 | 12/2007 | Tu et al. | |
| 2007/0293807 A1 | 12/2007 | Lynch et al. | |
| 2007/0298068 A1 | 12/2007 | Badawi et al. | |
| 2008/0015488 A1 | 1/2008 | Tu et al. | |
| 2008/0045878 A1 | 2/2008 | Bergheim et al. | |
| 2008/0058704 A1 | 3/2008 | Hee et al. | |
| 2008/0228127 A1 | 9/2008 | Burns et al. | |
| 2009/0005852 A1 | 1/2009 | Gittings et al. | |
| 2009/0028953 A1 | 1/2009 | Yamamoto et al. | |
| 2009/0030363 A1 | 1/2009 | Gellman | |
| 2009/0030381 A1 | 1/2009 | Lind et al. | |
| 2009/0043321 A1 | 2/2009 | Conston et al. | |
| 2009/0069786 A1 | 3/2009 | Vesely et al. | |
| 2009/0104248 A1 | 4/2009 | Rapacki et al. | |
| 2009/0138081 A1 | 5/2009 | Bergheim et al. | |
| 2009/0182421 A1 | 7/2009 | Silvestrini et al. | |
| 2009/0281520 A1 | 11/2009 | Highley et al. | |
| 2010/0004580 A1 | 1/2010 | Lynch et al. | |
| 2010/0057072 A1 | 3/2010 | Roman et al. | |
| 2010/0121342 A1 | 5/2010 | Schieber et al. | |
| 2010/0173866 A1 | 7/2010 | Hee et al. | |
| 2010/0222733 A1 | 9/2010 | Schieber et al. | |
| 2010/0234726 A1 | 9/2010 | Sirimanne et al. | |
| 2010/0234790 A1 | 9/2010 | Tu et al. | |
| 2011/0009874 A1 | 1/2011 | Wardle et al. | |
| 2011/0009958 A1 | 1/2011 | Wardle et al. | |
| 2011/0319806 A1 | 12/2011 | Wardle | |
| 2012/0010702 A1 | 1/2012 | Stegmann et al. | |
| 2012/0179087 A1 | 7/2012 | Schieber et al. | |
| 2012/0323159 A1 | 12/2012 | Wardle et al. | |
| 2013/0006165 A1 | 1/2013 | Euteneuer et al. | |

FOREIGN PATENT DOCUMENTS

| | | |
|---|---|---|
| DE | 19840047 A1 | 3/2000 |
| EP | 1615604 B1 | 8/2009 |
| EP | 2193821 A1 | 6/2010 |
| EP | 1715827 B1 | 12/2010 |
| EP | 2380622 A1 | 10/2011 |
| EP | 2468327 A1 | 6/2012 |
| EP | 2471563 A1 | 7/2012 |
| EP | 1833440 B1 | 8/2012 |
| JP | 11123205 | 5/1999 |
| JP | 2007181714 | 7/2007 |
| WO | WO 00/07525 A1 | 2/2000 |
| WO | WO 00/64389 A1 | 11/2000 |
| WO | WO 00/64393 A1 | 11/2000 |
| WO | WO 01/97727 A1 | 12/2001 |
| WO | WO 02/36052 A1 | 5/2002 |
| WO | WO 02/074052 A2 | 9/2002 |
| WO | WO 02/080811 A2 | 10/2002 |
| WO | WO 03/015659 A2 | 2/2003 |
| WO | WO 03/045290 A1 | 6/2003 |
| WO | WO 2004/093761 A1 | 11/2004 |
| WO | WO 2005/105197 A2 | 11/2005 |
| WO | WO 2006/066103 A2 | 6/2006 |
| WO | WO 2007/035356 A2 | 3/2007 |
| WO | WO 2007/047744 A2 | 4/2007 |
| WO | WO 2007/087061 A2 | 8/2007 |
| WO | WO2008/002377 A1 | 1/2008 |

OTHER PUBLICATIONS

Schieber et al.; U.S. Appl. No. 11/860,318 entitled "Ocular implants," filed Sep. 24, 2007.

Schieber et al.; U.S. Appl. No. 12/236,225 entitled "Ocular implants with asymmetric flexibility," filed Sep. 23, 2008.

Schieber et al.; U.S. Appl. No. 12/236,254 entitled "Ocular implant architectures," filed Sep. 23, 2008.

Bahler, et al.; Trabecular bypass stents decrease intraocular pressure in cultured human anterior segments; Amer. Journal of Ophthalmology; vol. 138, No. 6; pp. 988-994.e2; Dec. 2004.

D'Ermo, et al.; Our results with the operation of ab externo trabeculotomy; Ophthalmologica; vol. 163; pp. 347-355; 1971.

Johnstone et al.; "Microsurgery of Schlemm's Canal and the Human Aqueous Outflow System;" American Journal of Ophthalmology, vol. 76 (6): 906-917; Dec. 1973.

Lee et al.; Aqueous-venous shunt and intraocular pressure. Preliminary report of animal studies; Investigative Ophthalmology; vol. 5; No. 1; pp. 59-64; Feb. 1966.

Mäepea et al.; The pressures in the episcleral veins, schlemm's canal and the trabecular meshwork in monkeys: effects of changes in intraocular pressure; Exp. Eye Res.; vol. 49; pp. 645-663; 1989.

Savage, James; Gonioscopy in the management of glaucoma; Am. Academy of Ophthalmology; Focal Points; vol. XXIV; No. 3; pp. 1-14; Mar. 2006.

Schultz, Jared; Canaloplasty procedure shows promise for open-angle glaucoma in European study; Ocular Surgery News; vol. 34; Mar. 1, 2007.

Spiegel et al.; Schlemm's canal implant: a new method to lower intraocular pressure in patients with POAG?; Ophthalmic Surgery and Lasers; vol. 30; No. 6; pp. 492-494; Jun. 1999.

Ellingsen et al.; Trabeculotomy and sinusotomy in enucleated human eyes; Investigative Ophthalmology; vol. 11; pp. 21-28; Jan. 1972.

Grant; Experimental aqueous perfusion in enucleated human eyes; Archives of Ophthalmology; vol. 69; pp. 783-801; Jun. 1963.

Smit et al.; Effects of viscoelastic injection into schlemm's canal in primate and human eyes; J. Am. Academy of Ophthalmology; vol. 109; No. 4; pp. 786-792; Apr. 2002.

Euteneuer et al.; U.S. Appl. No. 12/398,847 entitled "Methods and Apparatus for Treating Glaucoma," filed Mar. 5, 2009.

Wardle et al.; U.S. Appl. No. 12/911,451 entitled "Ocular Implant System and Method," filed Oct. 25, 2010.

Moses, Robert; The effect of intraocular pressure on resistance to outflow; Survey of Ophthalmology; vol. 22; No. 2; pp. 88-100; Sep.-Oct. 1977.

Rosenquist et al.; Outflow resistance of enucleated human eyes at two different perfusion pressures and different extents of trabeculotomy; Current Eye Res.; vol. 8; No. 12; pp. 1233-1240; Dec. 1989.

Wardle et al.; U.S. Appl. No. 13/330,592 entitled "Delivering Ocular Implants Into the Eye," filed Dec. 19, 2011.

* cited by examiner

OCULAR IMPLANT DELIVERY SYSTEM AND METHOD

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention relates generally to devices that are implanted within the eye and delivery systems for such devices. More particularly, the present invention relates to delivery system for devices that facilitate the transfer of fluid from within one area of the eye to another area of the eye.

BACKGROUND OF THE INVENTION

According to a draft report by The National Eye Institute (NEI) at The United States National Institutes of Health (NIH), glaucoma is now the leading cause of irreversible blindness worldwide and the second leading cause of blindness, behind cataract, in the world. Thus, the NEI draft report concludes, "it is critical that significant emphasis and resources continue to be devoted to determining the pathophysiology and management of this disease." Glaucoma researchers have found a strong correlation between high intraocular pressure and glaucoma. For this reason, eye care professionals routinely screen patients for glaucoma by measuring intraocular pressure using a device known as a tonometer. Many modern tonometers make this measurement by blowing a sudden puff of air against the outer surface of the eye.

The eye can be conceptualized as a ball filled with fluid. There are two types of fluid inside the eye. The cavity behind the lens is filled with a viscous fluid known as vitreous humor. The cavities in front of the lens are filled with a fluid know as aqueous humor. Whenever a person views an object, he or she is viewing that object through both the vitreous humor and the aqueous humor.

Whenever a person views an object, he or she is also viewing that object through the cornea and the lens of the eye. In order to be transparent, the cornea and the lens can include no blood vessels. Accordingly, no blood flows through the cornea and the lens to provide nutrition to these tissues and to remove wastes from these tissues. Instead, these functions are performed by the aqueous humor. A continuous flow of aqueous humor through the eye provides nutrition to portions of the eye (e.g., the cornea and the lens) that have no blood vessels. This flow of aqueous humor also removes waste from these tissues.

Aqueous humor is produced by an organ known as the ciliary body. The ciliary body includes epithelial cells that continuously secrete aqueous humor. In a healthy eye, a stream of aqueous humor flows out of the anterior chamber of the eye through the trabecular meshwork and into Schlemm's canal as new aqueous humor is secreted by the epithelial cells of the ciliary body. This excess aqueous humor enters the venous blood stream from Schlemm's canal and is carried along with the venous blood leaving the eye.

When the natural drainage mechanisms of the eye stop functioning properly, the pressure inside the eye begins to rise. Researchers have theorized prolonged exposure to high intraocular pressure causes damage to the optic nerve that transmits sensory information from the eye to the brain. This damage to the optic nerve results in loss of peripheral vision. As glaucoma progresses, more and more of the visual field is lost until the patient is completely blind.

In addition to drug treatments, a variety of surgical treatments for glaucoma have been performed. For example, shunts were implanted to direct aqueous humor from the anterior chamber to the extraocular vein (Lee and Scheppens, "Aqueous-venous shunt and intraocular pressure," *Investigative Opthalmology* (February 1966)). Other early glaucoma treatment implants led from the anterior chamber to a subconjunctival bleb (e.g., U.S. Pat. No. 4,968,296 and U.S. Pat. No. 5,180,362). Still others were shunts leading from the anterior chamber to a point just inside Schlemm's canal (Spiegel et al., "Schlemm's canal implant: a new method to lower intraocular pressure in patients with POAG?" *Ophthalmic Surgery and Lasers* (June 1999); U.S. Pat. No. 6,450,984; U.S. Pat. No. 6,450,984). Delivery and deployment systems for some glaucoma implants are described, e.g., in US 2007/0191863 and US 2007/0010827. Surgical devices for accessing Schlemm's canal are described, e.g., in US 2007/0073275 and US 2006/0149194.

SUMMARY OF THE INVENTION

The present invention relates generally to ocular implants (such as, e.g., those used for glaucoma treatment) and their delivery systems. In particular, the invention relates to ocular implants and their delivery systems useful to treat glaucoma.

New glaucoma treatment implants are described in commonly assigned U.S. Ser. No. 11/860,318, "Ocular Implants," filed Sep. 24, 2007, the disclosure of which is incorporated herein. Prior ocular implant delivery systems cannot effectively be used to deliver and deploy the implants described therein. In addition, delivery systems used to deliver and deploy earlier glaucoma treatment implants fail to address certain delivery system needs.

On aspect of the invention provides a method of inserting an ocular implant into a patient's eye, the ocular implant being mounted on a carrier, with the method including the following steps: inserting a cannula into an anterior chamber of the eye; moving a distal exit port of the cannula into communication with Schlemm's canal; and advancing the ocular implant and carrier through an exit port of the cannula into Schlemm's canal. In embodiments in which the ocular implant has a plurality of openings, the method further includes the step of advancing the ocular implant and carrier into Schlemm's canal with the carrier blocking the implant openings.

In some embodiments, the inserting step includes the step of inserting the cannula through a cornea of the eye. In some embodiments, the passing step includes the step of advancing the ocular implant with a handheld actuator disposed exterior to the eye.

In some embodiments, the advancing step includes the step of moving a blunt distal surface into Schlemm's canal. The advancing step may also include the step of extending the ocular implant 60°-180° around Schlemm's canal.

In some embodiments, the method includes the step of rotating the implant within Schlemm's canal. Some embodiments of the method include the step of disengaging the ocular implant from the carrier, such as by moving at least one of the carrier and the ocular implant with respect to the other by, e.g., applying a distally directed force on the implant while applying a proximally directed force on the carrier. The step of applying a distally directed force may include the step of applying a distally directed force on the ocular implant with a pusher disposed in the cannula.

In some embodiments in which the carrier has a reduced diameter portion, the disengaging step may include the step of orienting the ocular implant with respect to the reduced diameter portion of the carrier. The advancing step may also include the step of advancing the ocular implant with a pusher having an implant engagement mechanism, in which case the disengaging step includes the step of orienting the ocular implant and an implant engagement mechanism of the pusher with respect to the reduced diameter portion of the carrier.

Some embodiments include the step of removing the carrier from the eye. The method may also include the step of ceasing advancement of the implant into Schlemm's canal when a proximal portion of the implant remains in the anterior chamber and a distal portion of the implant lies in Schlemm's canal. The method may also include the delivery of material through the carrier into Schlemm's canal.

Another aspect of the invention provides an ocular implant and delivery system having a cannula with a distal exit port adapted to be inserted into a Schlemm's canal portion of an eye; an ocular implant; a carrier disposed within the implant and movable with the implant within the cannula; and a proximal control adapted to be operated from exterior to an eye to move at least one of the carrier and the implant when the distal exit port of the cannula is within the eye.

In some embodiments, the ocular implant has a plurality of openings and the carrier is oriented to block the openings. The ocular implant and carrier together may form a blunt distal end. In some embodiments, the cannula forms an arc of a circle having, e.g., a radius of curvature less than about 0.1 inches and may have a diameter less than about 0.03 inches.

In some embodiments, the carrier has a larger diameter portion and a smaller diameter portion, with the ocular implant being engaged with the larger diameter portion of the carrier. Such embodiments may also include a pusher disposed within the cannula and engaged with the ocular implant, the pusher being operably connected to the proximal control. The pusher may have an implant engagement mechanism adapted to hold an ocular implant during advancement out of the exit port of the cannula. The ocular implant may be engaged with the implant engagement mechanism when the implant is disposed between the larger diameter portion of the carrier and the implant engagement mechanism, and the ocular implant may be disengaged with the implant engagement mechanism when the implant is disposed between the smaller diameter portion of the carrier and the implant engagement mechanism.

In some embodiments, the carrier has a material delivery lumen in communication with a material inlet in the proximal control.

In some embodiments, the proximal control has a distal handle connected to the cannula and a proximal handle with a carrier movement actuator, the proximal handle and the distal handle being movable with respect to each other. The proximal handle may also have an implant movement actuator.

Another aspect of the invention provides a method of inserting an ocular implant into a patient's eye including the following steps: inserting a cannula into an anterior chamber of the eye; moving a distal cutting portion of the cannula through trabecular meshwork into Schlemm's canal until a cannula stop element engages the trabecular meshwork; and passing the ocular implant through an exit port of the cannula into Schlemm's canal after engaging the stop element with the trabecular meshwork.

In some embodiments, the inserting step includes the step of inserting the cannula through a cornea of the eye. In some embodiments, the passing step includes the step of advancing the ocular implant with a handheld actuator disposed exterior to the eye.

In some embodiments, the passing step includes the step of moving a blunt distal surface into Schlemm's canal. The passing step may also include the step of extending the ocular implant 60°-180° around Schlemm's canal.

The method may also include one or more of the steps of rotating the implant within Schlemm's canal; maintaining forward pressure on the cannula while deforming at least a portion of the cannula during the passing step; and/or disengaging the ocular implant from a delivery tool. In some embodiments in which the delivery tool includes a pusher, the passing step includes the step of advancing a distal portion of the ocular implant through the exit port of the cannula with the pusher.

Some embodiments of the passing step include the step of advancing the implant into Schlemm's canal over a carrier. Such methods may also include the step of removing the carrier from the eye such as, e.g., by disengaging the ocular implant from the carrier. In some embodiments, material is delivered through the carrier into Schlemm's canal. Some embodiments of the invention also include the step of ceasing advancement of the implant into Schlemm's canal when a proximal portion of the implant remains in the anterior chamber and a distal portion of the implant lies in Schlemm's canal.

Yet another aspect of the invention provides an ocular implant system including a cannula with an implant lumen, a distal exit port, a distal cutting portion at least partially defining the exit port, and a stop element limiting passage of the distal cutting portion into an anatomical lumen at a point in which the exit port is within the lumen; and a proximal control adapted to be operated from exterior to an eye when the distal exit port of the cannula is within the eye.

In some embodiments, the cannula forms an arc of a circle having, e.g., a radius of curvature less than about 0.1 inches and/or a diameter less than about 0.03 inches. The cutting portion may have a cutting edge angled with respect to a central axis of the cannula, with the cutting edge being at an angle of between about 10 degrees and about 80 degrees with respect to the central axis in some embodiments. Some embodiments may also have the stop element disposed at a proximal extent of the cutting edge.

Some embodiments include a carrier disposed within the cannula and adapted to support an implant and sized to pass through the exit port. Such embodiments may also have an ocular implant engaged with the carrier. In embodiments in which the carrier has a larger diameter portion and a smaller diameter portion, the ocular implant may be engaged with the larger diameter portion of the carrier. The carrier may also have a material delivery lumen.

Some embodiments of the invention also include a pusher disposed within the cannula and engaged with the ocular implant, the pusher being operably connected to the proximal control. Such embodiments may also include an implant engagement mechanism adapted to hold an ocular implant during advancement out of the exit port of the cannula.

In some embodiments, the proximal control has a distal handle connected to the cannula and a proximal handle with a carrier movement actuator, the proximal handle and the distal handle being movable with respect to each other. The proximal handle may also have an implant movement actuator.

DETAILED DESCRIPTION OF THE INVENTION

The following detailed description should be read with reference to the drawings, in which like elements in different drawings are numbered identically. The drawings, which are not necessarily to scale, depict exemplary embodiments and are not intended to limit the scope of the invention. Examples of constructions, materials, dimensions, and manufacturing processes are provided for selected elements. All other elements employ that which is known to those of skill in the field of the invention. Those skilled in the art will recognize that many of the examples provided have suitable alternatives that can be utilized.

Figure 1:
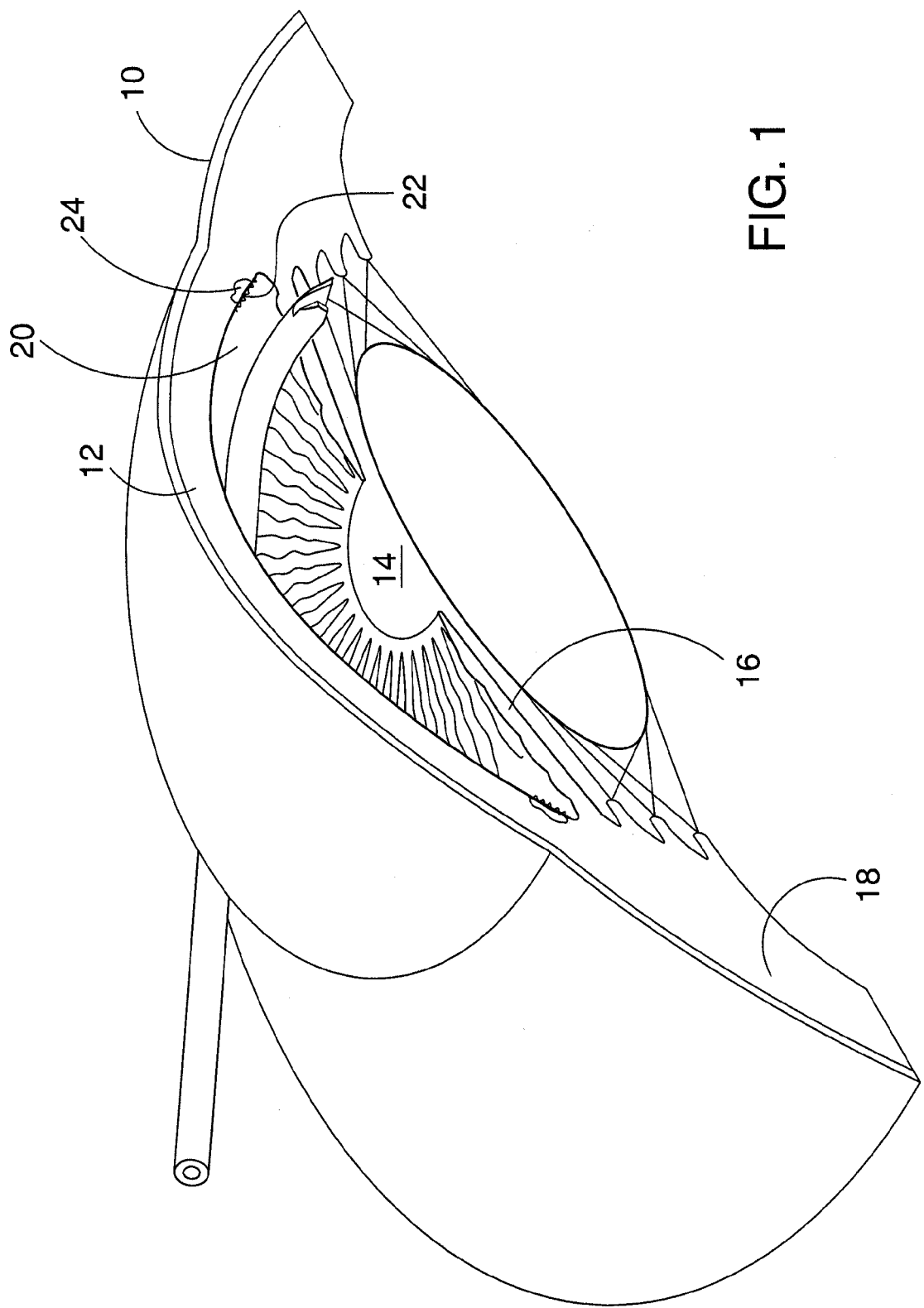
FIG. 1 shows a partial perspective and partial cross-sectional view of an eye.

FIG. 1 is a stylized depiction of a human eye 10 showing the cornea 12 covering the pupil 14 and iris 16 and the sclera 18 just beyond the iris. The anterior chamber 20 lies behind the cornea and in front of the pupil, iris and lens. As described above, in a healthy eye, aqueous humor flows out of the anterior chamber 20 through the trabecular meshwork 22 and into Schlemm's canal 24, located at the outer edge of the iris 16.

FIGS. 2-8 show an ocular implant 100 being delivered through a cannula 102 into Schlemm's canal 104. (Schlemm's canal is shown in these figures as being straight instead of curved for ease of illustration.) The ocular implant shown is described in more detail in U.S. Ser. No. 11/860,318, "Ocular Implants," filed Sep. 24, 2007. It should be understood that other ocular implants may be delivered and deployed by the delivery system of this invention.

Figure 2:
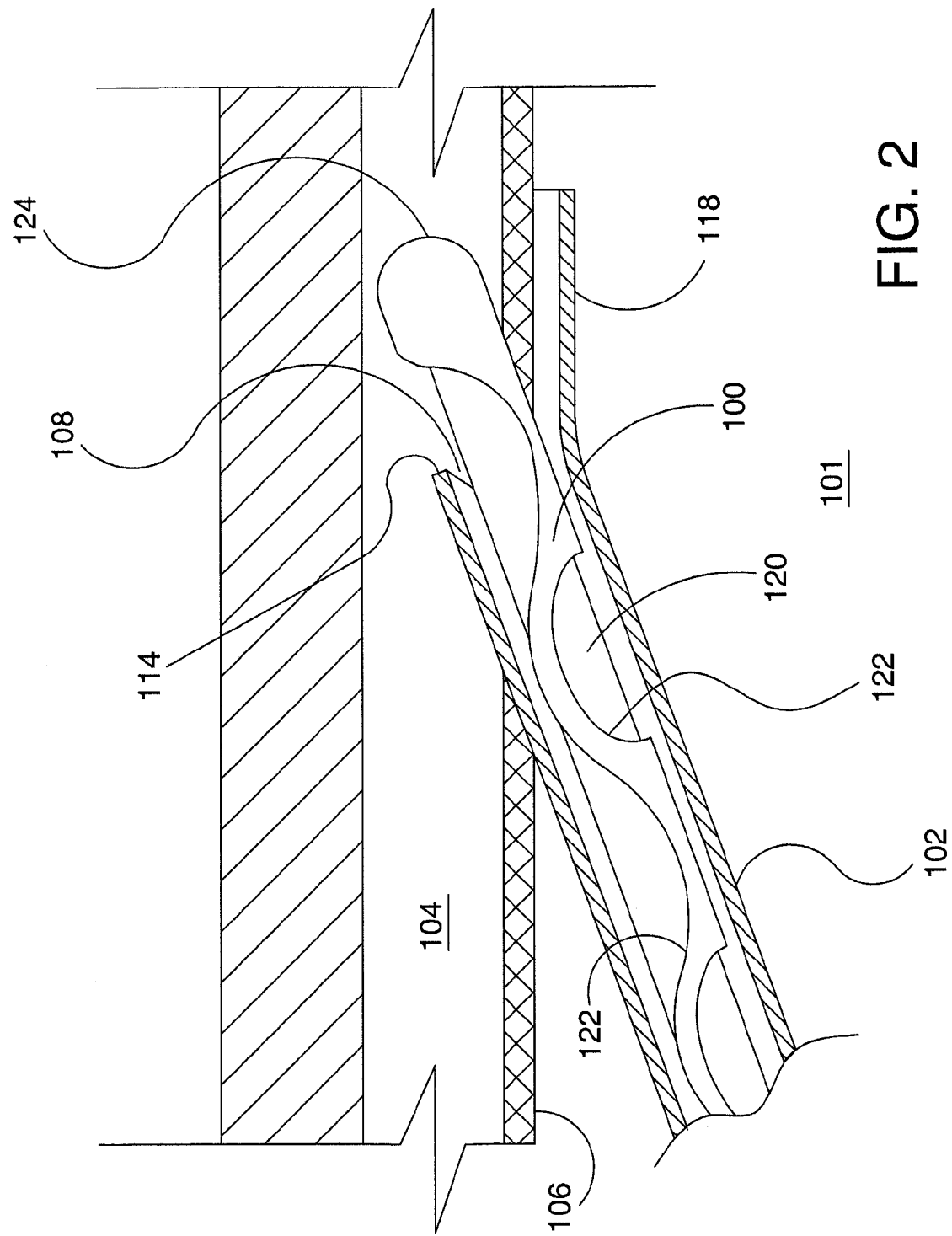
FIG. 2 is a partial cross-sectional view and a partial plan view showing an ocular implant being delivered into Schlemm's canal using a delivery system according to this invention.
Figure 3:
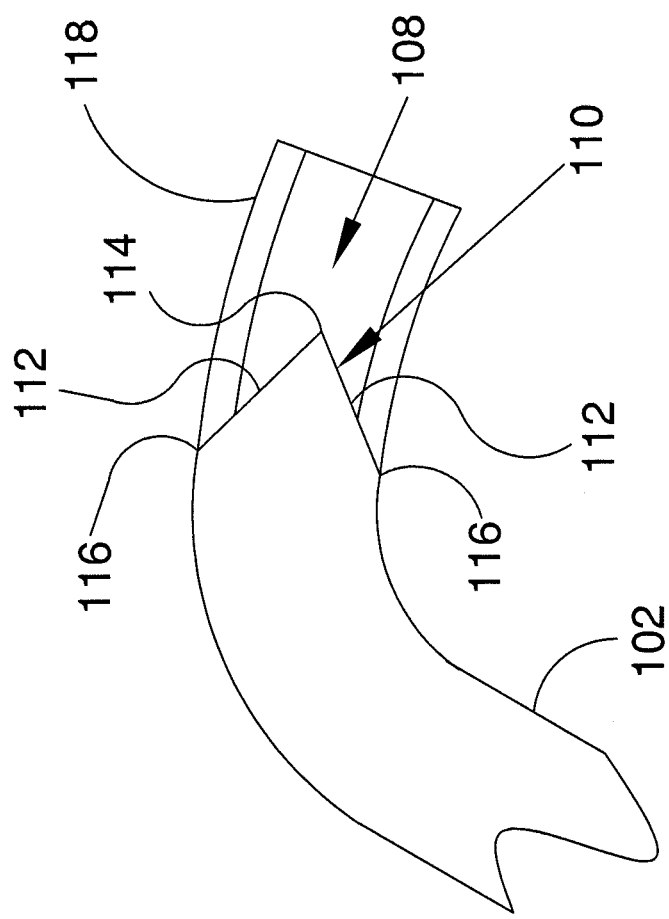
FIG. 3 is an elevational view of a portion of the cannula of the delivery system of FIG. 2.
Figure 4:
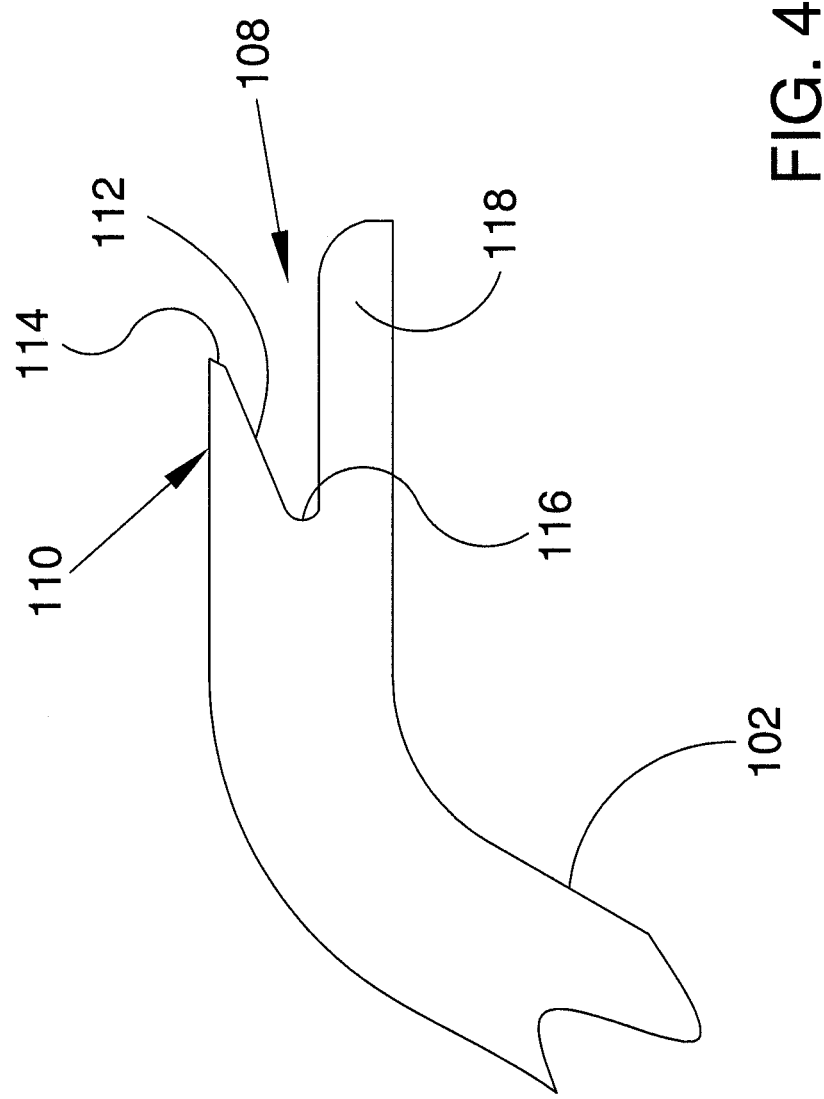
FIG. 4 is a side elevational view of a portion of the cannula of FIG. 3.
Figure 5:
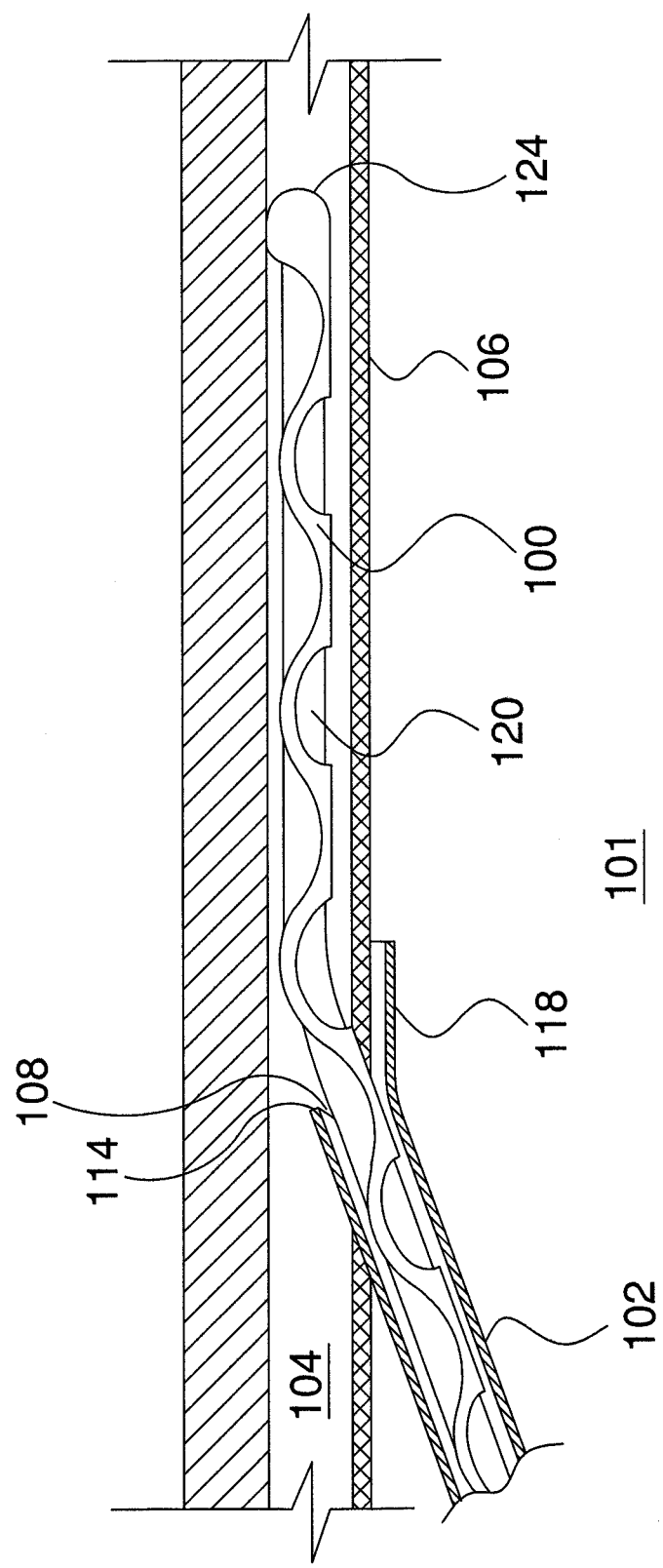
FIGS. 5 and 6 are further partial cross-sectional views and partial perspective views showing the ocular implant being delivered into Schlemm's canal using a delivery system according to the embodiment of FIG. 2.

As shown in FIG. 2, a distal portion of cannula 102 has passed through the cornea to be within the anterior chamber 101 of the eye and has pierced the trabecular meshwork 106 to enable a distal exit port 108 of cannula 102 to communicate with Schlemm's canal 104. In this embodiment, cannula 102 is a rigid curved tube that has a cutting portion 110 at the exit port 108, as shown in more detail in FIGS. 3 and 4. In some embodiments, cannula 102 is curved to achieve tangential entry into Schlemm's canal, such as by forming an arc of a circle having a radius of curvature less than about 0.1 inches. Other embodiments may have other shapes and curves.

In this embodiment, cutting portion 110 is formed from two convex edges 112 meeting at a tip 114. In other embodiments, the cutting edges can be concave or straight. As shown, edges 112 extend from tip 114 to a pair of optional stops 116 formed at the intersection of edges 112 with an optional cannula extension portion 118. As shown in FIG. 2, the distal end of cannula 102 may be advanced within the anterior chamber 101 toward the trabecular meshwork 106. When the distal end of cannula 102 meets the trabecular meshwork, tip 114 and edges 112 of cutting portion 110 are advanced to extend through the trabecular meshwork into Schlemm's canal while extension portion 118 bends back and remains within the anterior chamber 101. Distal movement of cannula 102 ceases when stops 116 engage the trabecular meshwork.

In some embodiments, cannula 102 is formed from transparent polycarbonate tubing having a diameter less than about 0.030 inches, e.g., an outer diameter of 0.028 inches and an inner diameter of 0.014 inches. In embodiments with cutting edges leading to stops, the cutting edges may be at angles of between about 10° and 80° with respect to the cannula's central axis, and the stops may be located approximately one-half diameter inward of tip 114. In embodiments with a cannula extension portion, the extension portion 118 may extend approximately 1.5 mm beyond tip 114. Among other functions, the bending of extension portion 118 while forward pressure is maintained on the cannula (as shown, e.g., in FIG. 2) provides feedback to the user of robust engagement with the trabecular meshwork and accurate positioning of the distal end of the cannula.

During delivery, ocular implant 100 is mounted on a carrier 120 which is movable with implant 100 within cannula 102. Among other functions, one particular function of carrier 120 is to block the openings 122 formed in implant 100 so as to minimize interference between the implant and tissue within Schlemm's canal 104 as the implant is advanced. The ocular implant 100 has a blunt distal end 124 in this embodiment to avoid damage to ocular tissue. In other embodiments, the blunt distal end may be provided at least in part by the carrier.

Figure 6:
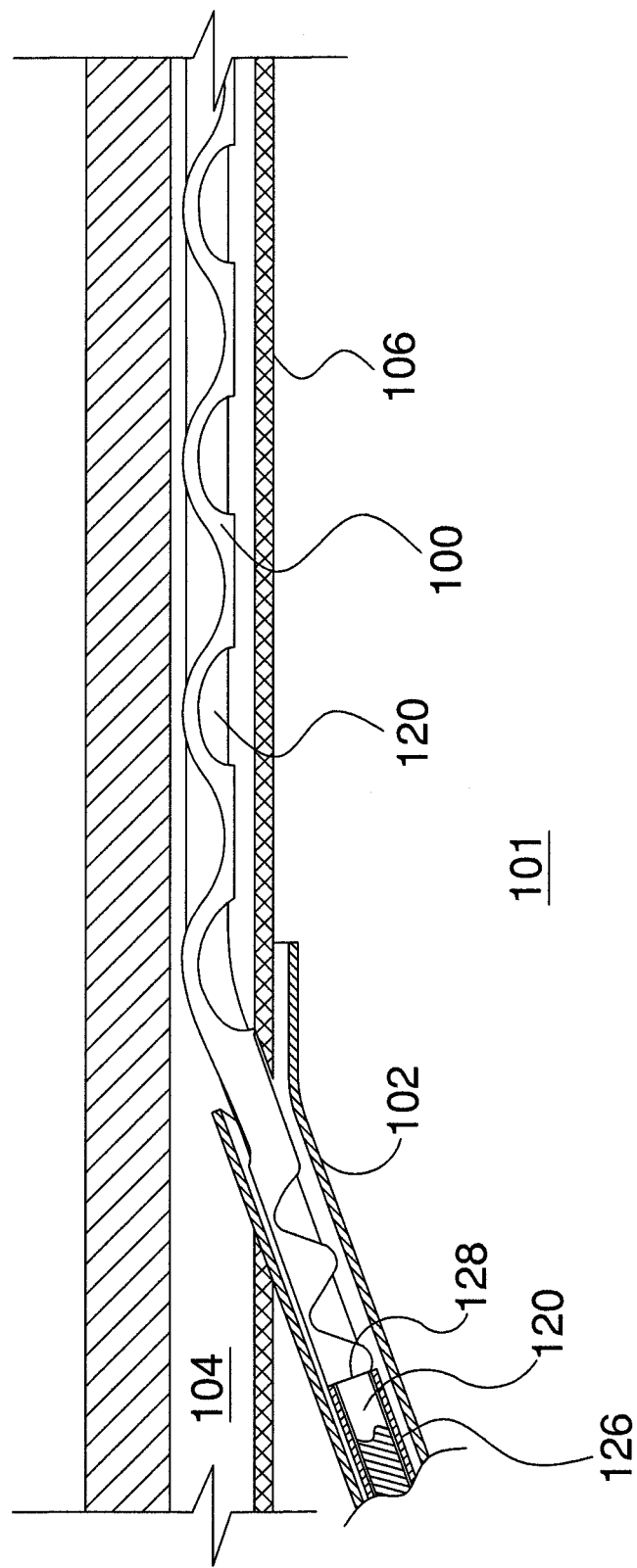

In this embodiment, a pusher 126 is engaged with the proximal end 128 of ocular implant 100, as shown in FIG. 6, to advance the implant through the exit port 108 of cannula 102 and into Schlemm's canal. Carrier 120 extends proximally into pusher 126 to, e.g., a handheld actuator (not shown) exterior to the eye.

Figure 7:
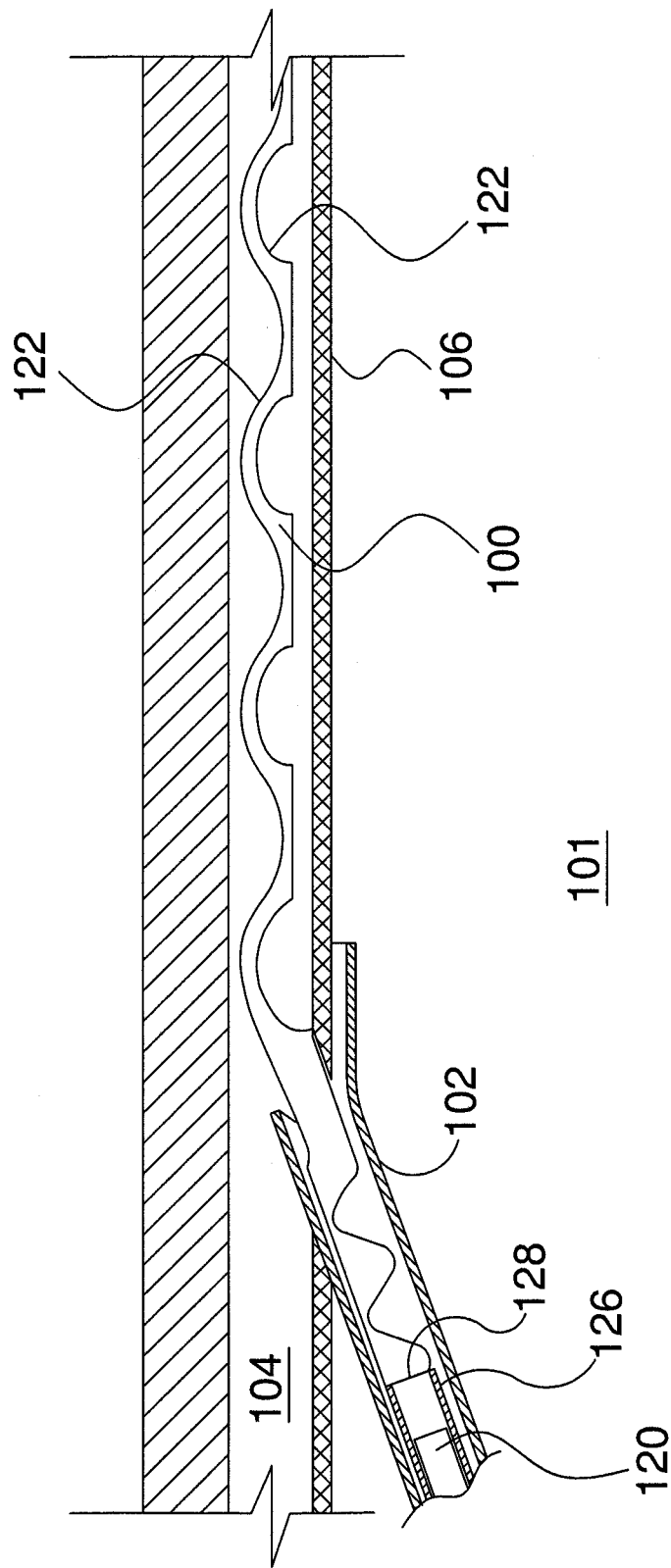
FIG. 7 is a partial cross-sectional view and a partial plan view showing the ocular implant and delivery system of FIG. 2 with the implant in place within Schlemm's canal and disengaged from a carrier of the delivery system.

When only the proximal end 128 of implant 100 remains in the anterior chamber 101, advancement of the implant into Schlemm's canal ceases. Depending on the design of the ocular implant, the implant may extend 60°-180° around Schlemm's canal at this point. Also, at this time or prior to it, the implant may be rotated within Schlemm's canal to attain the appropriate orientation. A proximal force can then be applied to carrier 120 (by, e.g., an external actuator or control) to withdraw the carrier proximally from the implant 100 while pusher 126 applies a distally directed force (once again by, e.g., an external actuator or control) to hold implant 100 in place, as shown in FIG. 7. Carrier 120 pusher 126 and cannula 102 may then be withdrawn from the eye, leaving the implant in Schlemm's canal with its proximal inlet end 128 within the anterior chamber 101.

Figure 8:
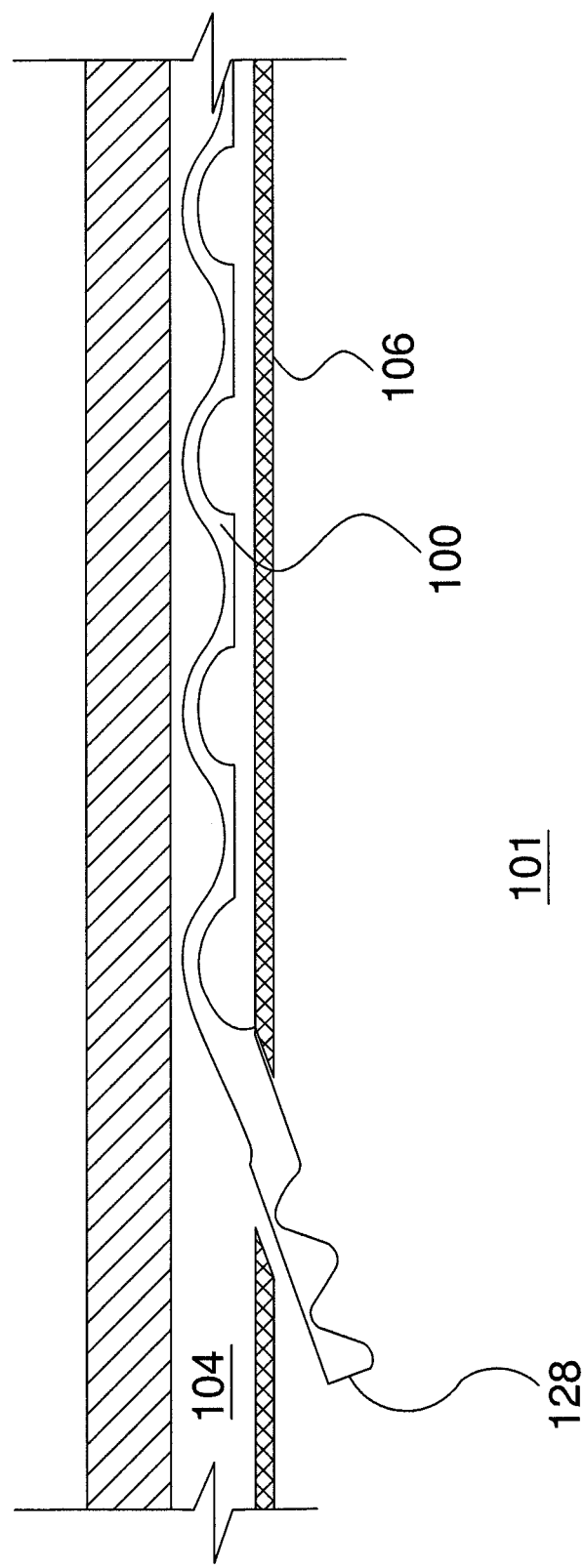
FIG. 8 is a partial cross-sectional view and a partial plan view of an implant in place within Schlemm's canal after delivery.
Figure 9:
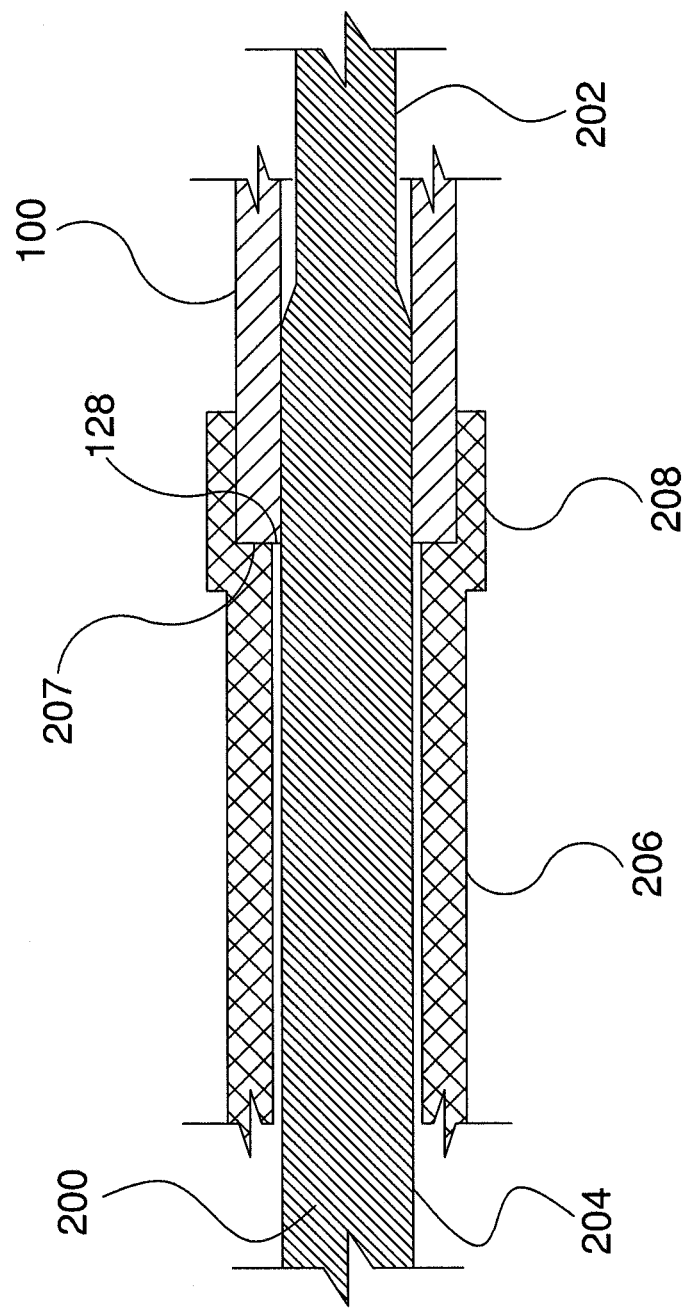
FIG. 9 is a cross-sectional view of a connection between an ocular implant and its delivery system according to one embodiment of the invention.
Figure 10:
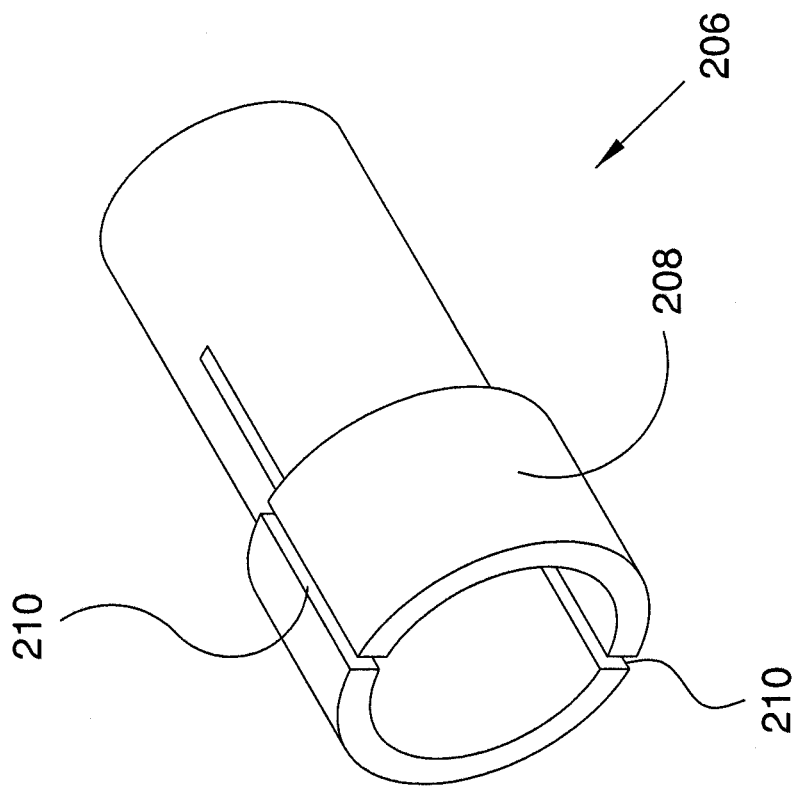
FIG. 10 is a perspective view of a portion of a delivery system pusher according to the embodiment of FIG. 9.
Figure 11:
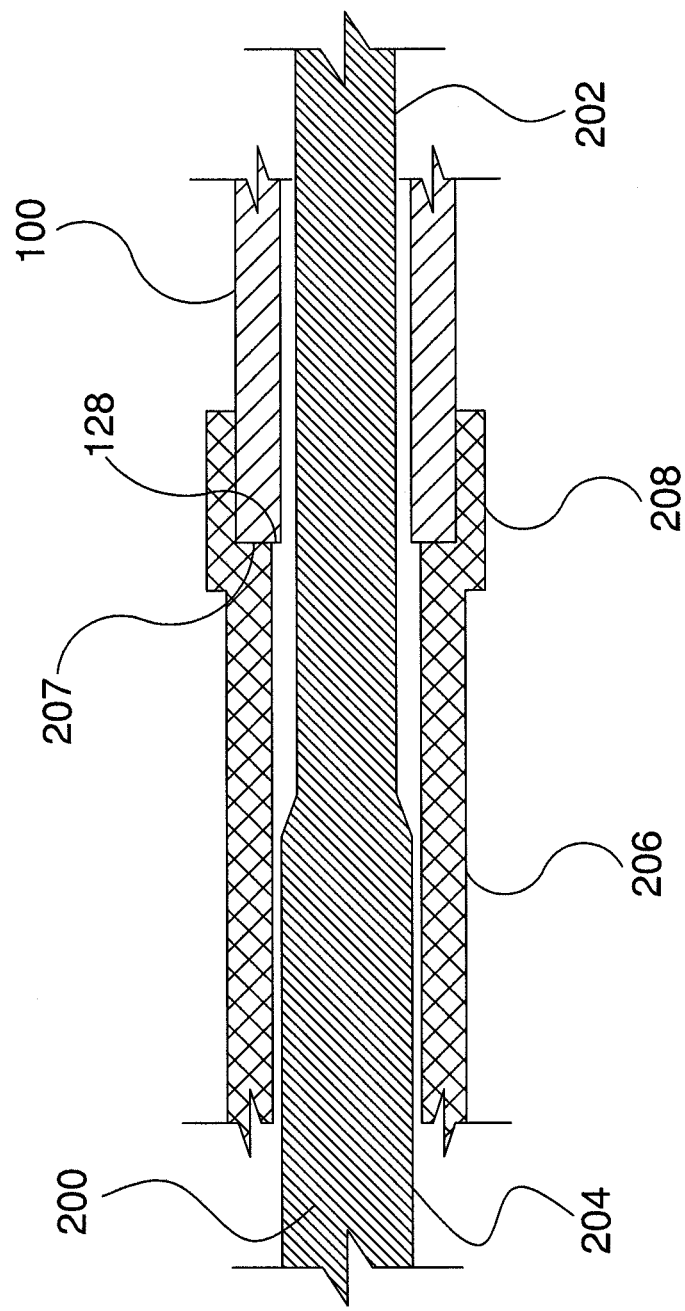
FIG. 11 is a partial cross-sectional view and a partial plan view of the ocular implant and delivery system of FIGS. 9 and 10 showing the implant disengaged from the delivery system.

FIGS. 9-11 show details of one embodiment of an engagement mechanism between an ocular implant (such as implant 100 shown in FIGS. 2-8) and a delivery system. In this embodiment, carrier 200 has a distal reduced diameter portion 202 and a proximal increased diameter portion 204. The distal end of pusher 206 has an inner lip 207 for engagement with the proximal end 128 of the implant and a collar surrounding the proximal end 128 of the implant. As shown in FIG. 10, one or more longitudinal slits 210 are formed in collar 208 to permit collar 208 to expand radially. In addition, the implant 100 of this embodiment has an open channel proximal end 128, as shown in FIG. 8, which can also be radially expanded. When in the engagement configuration shown in FIG. 9, the carrier's increased diameter portion 204 lies within the proximal end of implant 100, which in turn is disposed within collar 208 of pusher 206. The diameter of carrier portion 204 is larger than the at-rest diameters of collar 208 and implant portion 128, thereby causing collar 208 and implant portion 128 to radially expand from their at-rest shapes. When in this configuration, therefore, the pusher, implant and carrier have a friction fit that permits them to move as a unit.

To disengage the implant from the delivery system, carrier 200 is withdrawn proximally (or, alternatively, the implant is moved forward distally) until the reduced diameter portion 202 lies within the implant's proximal portion 128 and collar 208, as shown in FIG. 11. Since the diameter of reduced diameter portion 202 is less than the at-rest inner diameter of the implant's proximal portion 128, the implant is released from the delivery system carrier. The pusher can then be disengaged from the implant by simply withdrawing the pusher proximally.

Figure 12:
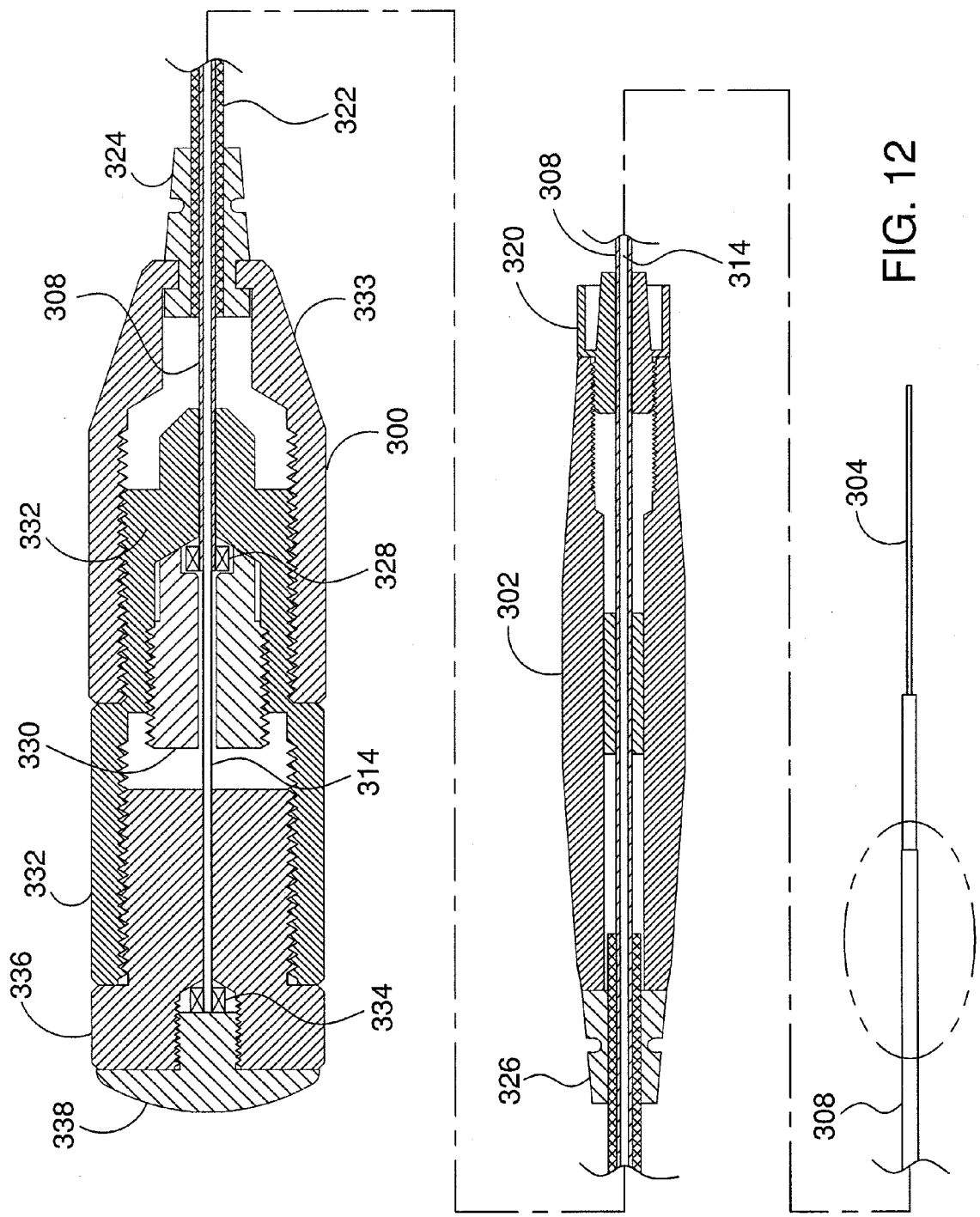
FIG. 12 is a partial cross-sectional view and a partial plan view of aspects of an ocular implant delivery system according to one embodiment of the invention.
Figure 13:
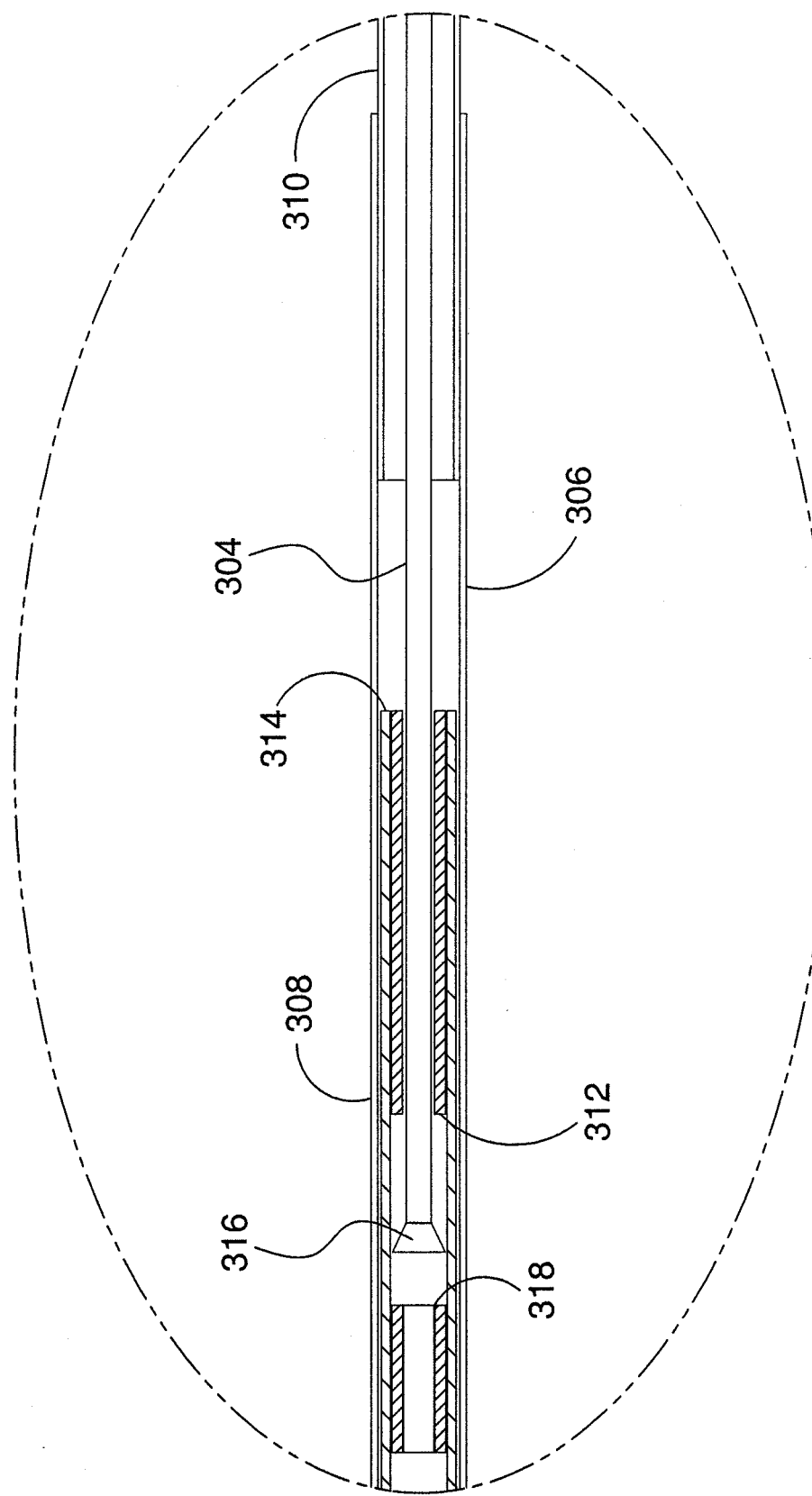
FIG. 13 is a partial cross-sectional view and a partial plan view of the portion of the delivery system of FIG. 12 indicated by "A".

FIGS. 12 and 13 show an embodiment of a handheld actuator of the implant and delivery system of this invention. In this embodiment, the actuator functions are divided between two handles, proximal handle 300 and distal handle 302. For ease of illustration, FIGS. 12 and 13 omit the cannula and implant. An ocular implant carrier 304 extends proximally through a pusher 306 into distal handle 302. In this embodiment, pusher 306 has a proximal push tube 308 and a distal reduced diameter push tube 310 bonded to the inside surface of proximal push tube 308. Carrier 304 also extends proximally through a distal sleeve 312 and through a distal portion of a proximal core tube 314. (Proximal core tube 314 is shown in a plan view in FIG. 12 and in cross-section in FIG. 13.) An enlarged proximal end 316 of carrier 304 is disposed within proximal core tube 314 between the proximal end of distal sleeve 312 and a distal stop element 318. The enlarged end 316 of carrier 304 is larger than the inner diameters of sleeve 312 and stop element 318. Thus, carrier 304 can move longitudinally only a limited amount with respect to proximal core tube 314.

A luer fitting 320 (or other suitable connector) at the distal end of distal handle 302 is provided to engage with the proximal end of a cannula (not shown), such as the cannula described above. Advancement of a cannula and implant into a patient's eye can therefore be controlled by movement of distal handle 302 with respect to the eye. In some embodiments, the exterior surface of proximal push tube 308 has at least one flat surface (such as a hexagonal surface) that mates with a corresponding shape on the inner surface of distal handle 302 so that rotation of handle 302 with respect to the cannula rotates the pusher and the implant.

A braided tube 322 extends proximally from a proximal end of distal handle 302 to a distal end of proximal handle 300 through distal and proximal strain relief portions 324 and 326, respectively. Braided tube 322 permits handles 300 and 302 to be rotated with respect to each other, thereby preventing any unintentional rotation of handle 300 from rotating handle 302.

Proximal push tube 308 extends proximally through distal handle 302 and braided tube 322 to a push tube stop 328 within proximal handle 300, to which it is bonded. Stop 328 is held in place within a push tube actuator 332 by a plug 330. In this embodiment, stop 328 and proximal push tube 308 are free to rotate relative to push tube actuator 332. Push tube actuator 332 has exterior threads mating with interior threads of a stationary handle portion 333. Proximal core tube 314 extends further proximally beyond proximal push tube 308 to a core tube stop 334, to which it is bonded. Stop 334 is held in place within a core tube actuator 336 by a domed plug 338. In this embodiment, stop 334 and core proximal core tube 314 are free to rotate relative to core tube actuator 336. Core tube actuator 336 has exterior threads mating with interior threads of push tube actuator 332.

The two handle design of this embodiment permits two person operation of the ocular implant and delivery system. In use, an ocular implant (such as that described above) is mounted on carrier 304 and placed within a cannula (such as that described above) attached to luer fitting 320 of distal handle 302. Under visual observation using a goniolens, a surgeon advances the distal end of the cannula through an opening in the patient's cornea into the anterior chamber of the eye by advancing distal handle 302. When the cannula has cut through the trabecular meshwork to place the cannula's distal exit port into communication with Schlemm's canal, an assistant holding proximal handle 300 advances the carrier and implant out of the cannula's distal exit port by simultaneously turning actuators 332 and 336, which, due to the mating threads of actuator 332 and handle portion 333, moves push tube 308 and carrier 304 distally with respect to handle portion 333, distal handle 302 and the cannula.

When the implant has been advanced a sufficient distance into Schlemm's canal, the implant is disengaged from the delivery system by turning actuator 336 with respect to actuator 332 to move the carrier 304 proximally with respect to the push tube 308, thereby keeping the implant stationary while the carrier is withdrawn. After the implant has been deployed and disengaged from the delivery system, the pusher, carrier and cannula are removed from the patient's eye.

Figure 14:
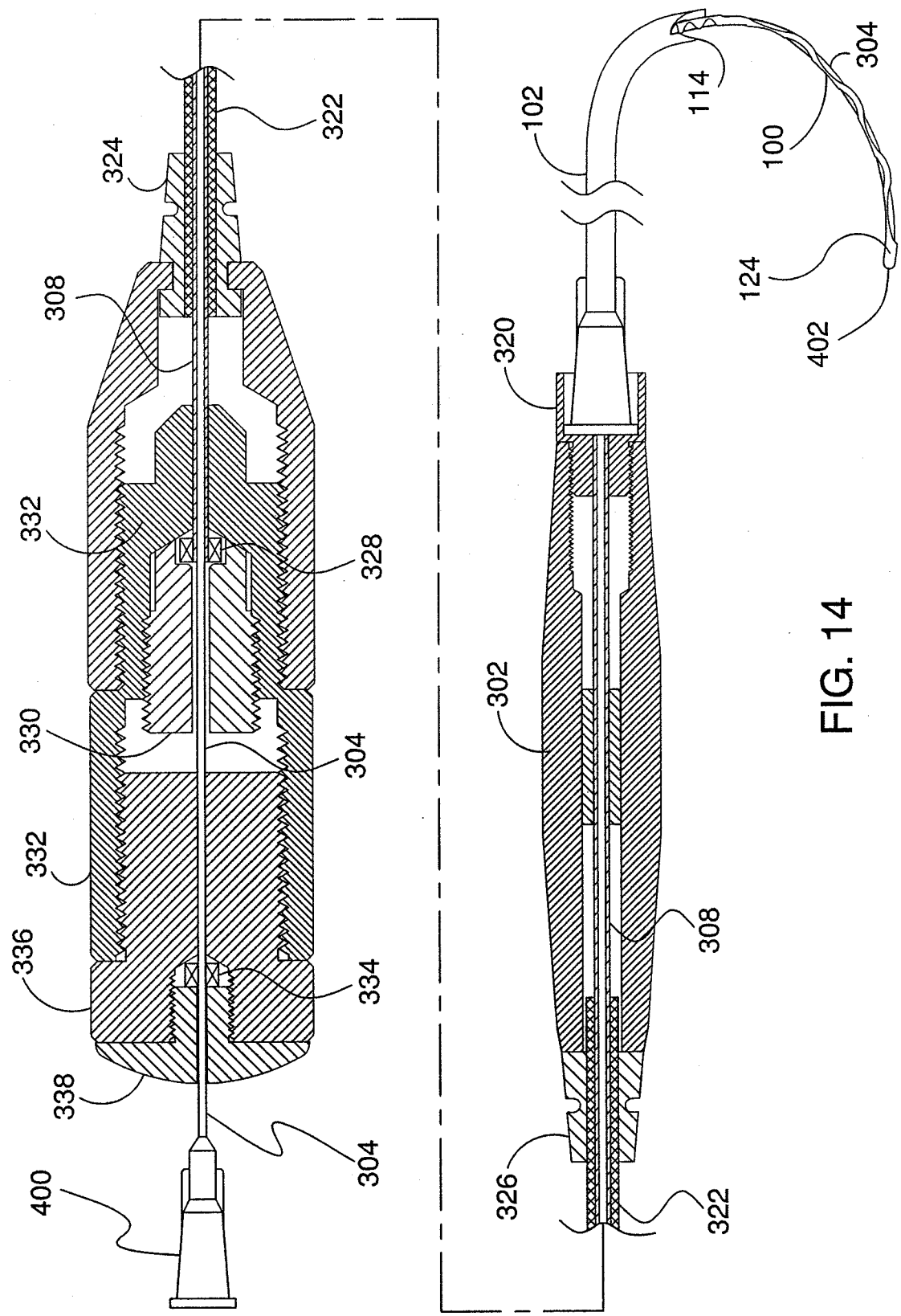
FIG. 14 is a partial cross-sectional view and a partial plan view of an ocular implant delivery system and ocular implant according to another embodiment of the invention.

FIG. 14 shows yet another embodiment of an ocular implant and delivery system according to the invention. (Elements similar to that of earlier embodiments are given the same element numbers.) This embodiment omits the proximal core tube interacting with the carrier. Instead, the carrier 304 extends proximally through dome plug 338 to a proximal fitting 400 (such as a luer fitting) having in inlet 401 in communication with a central lumen of carrier 304. The ocular implant of this embodiment has a distal exit port 402 lined up with the central lumen of carrier 304. Materials (such as dye, contrast agent, drugs, etc.) can be injected through proximal fitting 400 into carrier 304 and out of the distal exit port 402 of implant 100 into the patient's eye, as needed. As in the earlier embodiment, when the implant has been advanced a sufficient distance into Schlemm's canal, the implant is disengaged from the delivery system by turning actuator 336 with respect to actuator 332 to move the carrier 304 proximally with respect to the push tube 308, thereby keeping the implant stationary while the carrier is withdrawn. After the implant has been deployed and disengaged from the delivery system, the pusher, carrier and cannula are removed from the patient's eye. In some embodiments, implant 100 can be rotated by rotating proximal fitting 400 and carrier 304.

What is claimed is:

1. An ocular implant and delivery system comprising:
a cannula comprising a distal cutting portion, a distal exit port adapted to be inserted into a Schlemm's canal portion of an eye, and a distal stop element;
an ocular implant disposed within the cannula and comprising a plurality of openings through a longitudinal side of the implant;
a pusher disposed within the cannula and engaged with the ocular implant; and
a proximal control operably connected to the pusher and adapted to be operated from exterior to an eye to move the implant when the distal exit port of the cannula is within the eye.

2. The system of claim 1 wherein the cannula forms an arc of a circle.

3. The system of claim 2 wherein the cannula has a radius of curvature less than about 0.1 inches.

4. The system of claim 1 wherein the cannula has a diameter less than about 0.03 inches.

5. The system of claim 1 wherein the cutting portion comprises a cutting edge angled with respect to a central axis of the cannula.

6. The system of claim 5 wherein the cutting edge is at an angle of between about 10 degrees and about 80 degrees with respect to the central axis.

7. The system of claim 5 wherein the stop element is disposed at a proximal extent of the cutting edge.

8. The system of claim 1 wherein the distal cutting portion at least partially defines the exit port.

9. The system of claim 1 further comprising a carrier disposed within the implant, oriented to block the implant openings and movable with the implant within the cannula.

10. The system of claim 9 wherein the ocular implant and carrier together comprise a blunt distal end.

11. The system of claim 9 wherein the carrier has a larger diameter portion and a smaller diameter portion, the ocular implant being engaged with the larger diameter portion of the carrier.

12. The system of claim 11 wherein the pusher comprises an implant engagement mechanism adapted to hold an ocular implant during advancement out of the exit port of the cannula.

13. The system of claim 12 wherein the ocular implant is engaged with the implant engagement mechanism when the implant is disposed between the larger diameter portion of the carrier and the implant engagement mechanism, and the ocular implant is disengaged with the implant engagement mechanism when the implant is disposed between the smaller diameter portion of the carrier and the implant engagement mechanism.

14. The system of claim 12 wherein the engagement mechanism comprises a friction fit between the implant and the carrier.

15. The system of claim 14 wherein the engagement mechanism further comprises a friction fit between the implant and the pusher.

16. The system of claim 12 wherein the engagement mechanism is adapted to attach the implant to the pusher such that the implant and pusher can be moved as a unit.

17. The system of claim 12 wherein the engagement mechanism is adapted to attach the implant to the pusher such that the implant, carrier and pusher can be moved as a unit.

18. The system of claim 9 wherein the carrier comprises a material delivery lumen in communication with a material inlet in the proximal control.

19. The system of claim 9 wherein the proximal control comprises a distal handle connected to the cannula and a proximal handle comprising a carrier movement actuator, the proximal handle and the distal handle being movable with respect to each other.

20. The system of claim 19 wherein the proximal handle further comprises an implant movement actuator.

21. The system of claim 9 wherein the carrier extends proximally into the pusher.

22. The system of claim 9 wherein the carrier is further adapted to move with the implant through the distal exit port of the cannula.

23. The system of claim 22 wherein the proximal control is further adapted to move the carrier through the distal exit port of the cannula and to retract the carrier back into the cannula.

24. The system of claim 1 wherein the distal cutting portion comprises two convex edges meeting at a tip.

* * * * *

UNITED STATES PATENT AND TRADEMARK OFFICE
CERTIFICATE OF CORRECTION

| | | |
|---|---|---|
| PATENT NO. | : 8,512,404 B2 | Page 1 of 1 |
| APPLICATION NO. | : 11/943289 | |
| DATED | : August 20, 2013 | |
| INVENTOR(S) | : Frion et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1076 days.

Signed and Sealed this
Twenty-fourth Day of February, 2015

Michelle K. Lee
*Deputy Director of the United States Patent and Trademark Office*